(12) United States Patent
Russell

(10) Patent No.: US 11,186,841 B2
(45) Date of Patent: Nov. 30, 2021

(54) COMPOSITIONS AND METHODS FOR INHIBITION OF THE LNCRNA SAF TO DRIVE APOPTOTIC CELL DEATH IN HUMAN IMMUNODEFICIENCY VIRUS (HIV) INFECTED HUMAN MACROPHAGES

(71) Applicant: Cornell University, Ithaca, NY (US)

(72) Inventor: David G. Russell, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/707,966

(22) Filed: Dec. 9, 2019

(65) Prior Publication Data
US 2020/0181621 A1    Jun. 11, 2020

Related U.S. Application Data

(60) Provisional application No. 62/776,789, filed on Dec. 7, 2018.

(51) Int. Cl.
  *C12N 15/113*    (2010.01)
  *C07K 14/16*    (2006.01)
  *A61P 31/18*    (2006.01)

(52) U.S. Cl.
  CPC .......... *C12N 15/1132* (2013.01); *A61P 31/18* (2018.01); *C07K 14/16* (2013.01); *C07K 2317/73* (2013.01); *C12N 2310/14* (2013.01)

(58) Field of Classification Search
  None
  See application file for complete search history.

(56) References Cited

PUBLICATIONS

Ponzoni et al. Int. J. Mol. Sci. 19, 1953, pp. 1-17 (Year: 2018).*
Lee et al. Expert Opin. Drug Deliv, 12:1009-1026 (Year: 2015).*
Boliar et al. PNAS 116, 7431-7438 (Year: 2019).*

* cited by examiner

*Primary Examiner* — Brian Whiteman
(74) *Attorney, Agent, or Firm* — Hodgson Russ LLP

(57) ABSTRACT

Provided are compositions and methods for prophylaxis or therapy for human immunodeficiency virus (HIV) infection. The compositions and methods involve use of RNAi agents targeted to an anti-apoptotic long non-coding RNA (lncRNA) that is lncRNA SAF (FAS-AS1) or HOXA-AS2. The RNAi agents preferentially induce apoptosis of HIV infected macrophages. RNAi agents, and macrophages containing the RNAi agents, are also provided.

5 Claims, 7 Drawing Sheets
(7 of 7 Drawing Sheet(s) Filed in Color)
Specification includes a Sequence Listing.

SEQUENCE LISTING

```
<160> NUMBER OF SEQ ID NOS: 14

<210> SEQ ID NO 1
<211> LENGTH: 25
<212> TYPE: DNA
<213> ORGANISM: artificial sequence
<220> FEATURE:
<223> OTHER INFORMATION: siRNA

<400> SEQUENCE: 1
ccgugaaggc auaaaagcaa acatt                                            25

<210> SEQ ID NO 2
<211> LENGTH: 27
<212> TYPE: RNA
<213> ORGANISM: artificial sequence
<220> FEATURE:
<223> OTHER INFORMATION: siRNA

<400> SEQUENCE: 2
aauguuugcu uuuaugccuu cacgguu                                          27

<210> SEQ ID NO 3
<211> LENGTH: 21
<212> TYPE: DNA
<213> ORGANISM: artificial sequence
<220> FEATURE:
<223> OTHER INFORMATION: primer

<400> SEQUENCE: 3
catctcagcc tcttggtgta a                                                21

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
atgggagata tgggattgaa c                                                21

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5
aagcactggg accaggagc                                                   19
```

```
<210> SEQ ID NO 6
<211> LENGTH: 24
<212> TYPE: DNA
<213> ORGANISM: artificial sequence
<220> FEATURE:
<223> OTHER INFORMATION: primer

<400> SEQUENCE: 6
tggtagctgg atttgttact tggc                                      24

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7
tagtgtgatt ggatggcctg c                                         21

<210> SEQ ID NO 8
<211> LENGTH: 20
<212> TYPE: DNA
<213> ORGANISM: artificial sequence
<220> FEATURE:
<223> OTHER INFORMATION: ACA AGC ATT GTT AGC TGC TG

<400> SEQUENCE: 8
acaagcattg ttagctgctg                                           20

<210> SEQ ID NO 9
<211> LENGTH: 20
<212> TYPE: DNA
<213> ORGANISM: artificial sequence
<220> FEATURE:
<223> OTHER INFORMATION: : GAC AAG CTT CCC GTT CTC AG

<400> SEQUENCE: 9
gacaagcttc ccgttctcag                                           20

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10
gagtcaacgg atttggtcgt                                           20

<210> SEQ ID NO 11
<211> LENGTH: 14
<212> TYPE: DNA
<213> ORGANISM: artificial sequence
<220> FEATURE:
<223> OTHER INFORMATION: primer

<400> SEQUENCE: 11
ctcgctttgg caca                                                 14

<210> SEQ ID NO 12
<211> LENGTH: 20
<212> TYPE: DNA
<213> ORGANISM: artificial sequence
<220> FEATURE:
<223> OTHER INFORMATION: primer
```

```
<400> SEQUENCE: 12
aacgcttcac gaatttgcgt                                               20

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
ggccctgtaa ttggaatgag tc                                            22

<210> SEQ ID NO 14
<211> LENGTH: 21
<212> TYPE: DNA
<213> ORGANISM: artificial sequence
<220> FEATURE:
<223> OTHER INFORMATION: primer

<400> SEQUENCE: 14
ccaagatcca actacgagct t                                             21
```

COMPOSITIONS AND METHODS FOR INHIBITION OF THE LNCRNA SAF TO DRIVE APOPTOTIC CELL DEATH IN HUMAN IMMUNODEFICIENCY VIRUS (HIV) INFECTED HUMAN MACROPHAGES

CROSS REFERENCE TO RELATED APPLICATIONS

This application claims priority to U.S. provisional patent application No. 62/776,789, filed Dec. 7, 2018, the entire disclosure of which is incorporated herein by reference.

STATEMENT REGARDING FEDERALLY SPONSORED RESEARCH OR DEVELOPMENT

This invention was made with government support under grants AI118582 and AI136097 awarded by The National Institutes of Health. The government has certain rights in the invention.

BACKGROUND

Cell death is a prominent feature of HIV-1 pathogenesis which is characterized by severe loss of T lymphocytes and other immune cells during the disease progression (1-6). Infection of activated $CD4^+$ T cells, the primary target of HIV-1, results in efficient and productive virus replication but rapidly leads to a virus-induced cytopathic death of the infected cells (7). The other cellular target of HIV-1 infection is macrophages (8). Tissue macrophages are terminally differentiated, long-lived cells that are maintained in their local tissue environment through self-renewal (9-12). These myeloid cells reside in various tissues and vary in their phenotype and functions depending upon their locations (13). Several tissue macrophages such as brain microglia, liver Kupffer cells and alveolar macrophages have long been recognized to harbor and support HIV-1/SIV infection at different stages of the disease (14-20). In fact, in a recent study, macrophages were shown to support HIV-1 replication and maintain plasma viremia even in the absence of T cells (21). However, unlike $CD4^+$ T cells, macrophages support relatively lower levels of HIV-1 replication and are largely resistant to virus-induced cell death (22-24). This unique ability of macrophages to sustain viral replication while retaining extended cell survival makes them an ideal candidate for viral persistence even during long-term ART therapy, which poses a major hurdle in the HIV-1 cure efforts. Without intending to be constrained by any particular theory, it is considered that a complex host-pathogen interaction must be in play to maintain such a delicate balance between productive HIV-1 infection and macrophage survival.

Apoptosis is the most common form of virus-induced programmed cell death and several studies have examined the mechanisms involved in induction or evasion of apoptosis by HIV-1 (25-27). These studies are mainly focused on the role of various protein modulators, either viral (HIV-1 Nef, Vpr, Tat and Env) or cellular (Fas, TNF-α, Bcl-2, Bax, FLICE, p53) factors (28-30). However, there is only limited information available on how HIV-1 infection affects non-protein-coding regulatory elements such as the long non-coding RNAs (lncRNA). lncRNAs are RNA transcripts that are larger than 200 nucleotides in length yet lack a protein-coding open reading frame. They are now known to play a significant role in regulating diverse cellular pathways both in health and disease, including viral infections such as HIV-1. The lncRNAs NEAT1 and NRON have been shown to inhibit HIV replication by regulating nuclear localization of viral transcripts (31, 32). Several lncRNAs modulate cell apoptotic pathway at both extrinsic and intrinsic levels. For instance, SAF (FAS-AS1) and HOXA-AS2 are anti-apoptotic lncRNAs that regulate death receptor functions in the extrinsic pathway, while the lncRNAs Malat1, GAS5 and MEG3 act on the intra-cellular regulator p53 to induce apoptosis (33-37). The possible role of such lncRNAs during HIV-1 infection has yet to be explored. Thus, there is an ongoing need for improved compositions and methods that relate to manipulating lncRNAs for therapeutic purposes. The present disclosure is related to this need.

SUMMARY

The present disclosure reveals the impact of the lncRNA SAF in regulation of apoptosis in macrophages, a long-lived cellular reservoir of HIV-1, that are vastly immune to virus-induced cell death. Based at least in part on this discovery, the disclosure provides compositions and methods for prophylaxis or therapy for a human immunodeficiency virus (HIV) infection. The methods generally comprise administering to an individual in need thereof an RNAi agent targeted to an anti-apoptotic long non-coding RNA (lncRNA) that is lncRNA SAF (FAS-AS1) or HOXA-AS2. Specific and non-limiting embodiments of RNAi agents include polynucleotides that comprise SEQ ID NO:1, SEQ ID NO:2, and duplexes comprising SEQ ID NO:1 and SEQ ID NO:2. In certain embodiments, the disclosure provides administering to the individual the RNAi agent into a population of macrophages in the individual, wherein macrophages in the population of macrophages comprising HIV infected macrophages. The HIV infected macrophages are selectively induced to undergo apoptosis. The disclosure also comprises HIV infected macrophages that contain an RNAi agent that is described further herein, such agents comprising a polynucleotide comprising the sequence of SEQ ID NO:1 and/or SEQ NO:2. Isolated RNAi agents, and pharmaceutical formulations comprising them are also provided. The RNAi agents are shown to function as small interfering RNA (siRNA), also referred to in the art as short interfering RNA or silencing RNA.

In more detail, the disclosure demonstrates that expression of SAF is significantly up-regulated in HIV-1 infected human monocyte-derived-macrophages (MDM) compared to bystander and virus non-exposed cells. A similar enhancement in SAF RNA expression is also detected in the virus infected, lung alveolar macrophages (AM) obtained from HIV-1 infected individuals. Down-regulation of SAF with siRNA treatment increases active caspase 3 level in virus infected MDMs. This induction of apoptosis occurs exclusively in HIV-1 infected macrophages but not in bystander cells, leading to a significant reduction in HIV-1 replication and overall viral burden in the macrophage culture. Thus, the disclosure provides for targeting of the lncRNA SAF as a way to specifically induce cell death in HIV-1 infected macrophages.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1. HIV-1 infection and apoptosis in MDMs. (A) Representative flow cytometry plots showing HIV-1 p24 staining of MDMs and demarcation of virus non-exposed (Green), virus exposed but uninfected bystander (Blue) and virus infected (Red) cells. (B) The percentage (mean±SEM) of HIV-1 infected MDMs was determined by flow cytometry staining with PE-conjugated anti-p24 antibody on day 1, 4, 8 and 11 post infection (n=4). (C-D) The percentage (mean±SEM) of viable (C) and active caspase 3 positive (D) MDMs was determined by flow cytometry staining with fixable viability dye eFluor506 and CellEvent caspase 3/7 green detection reagent, respectively within virus non-exposed (green), bystander (blue) and infected (red) cells at indicated days post infection (n=4).

Figure 2:
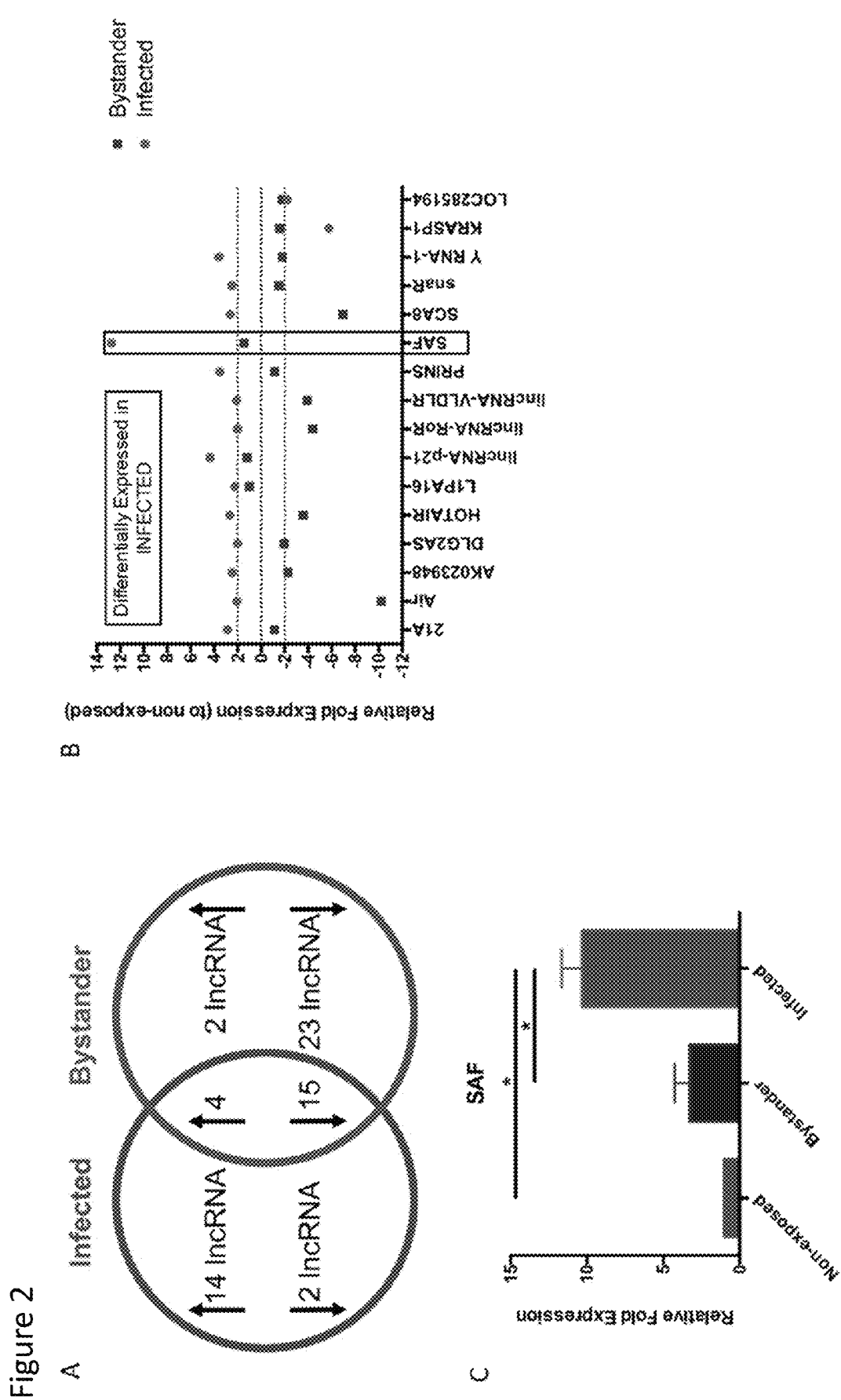

FIG. 2. lncRNA SAF expression in HIV-1 infected MDMs. (A) Venn diagram summarizing changes in lncRNA expression profile in HIV-1 infected and bystander cells compared to virus non-exposed MDMs. At least 2-fold up- or down-regulation compared to non-exposed MDMs was considered as a change in expression. (B) A summary of the relative expressions of the 16 lncRNAs that were differentially expressed in HIV-1 infected (red dot) MDMs compared to bystander (blue box) cells. The lncRNA SAF is identified with a box. (C) Fold changes (mean±SEM) in expression of the lncRNA SAF was determined by quantitative real-time PCR in non-exposed, bystander and virus infected MDMs (n=4). Significance of difference among groups determined by one-way ANOVA is indicated above the groups, *=p<0.05.

Figure 3:
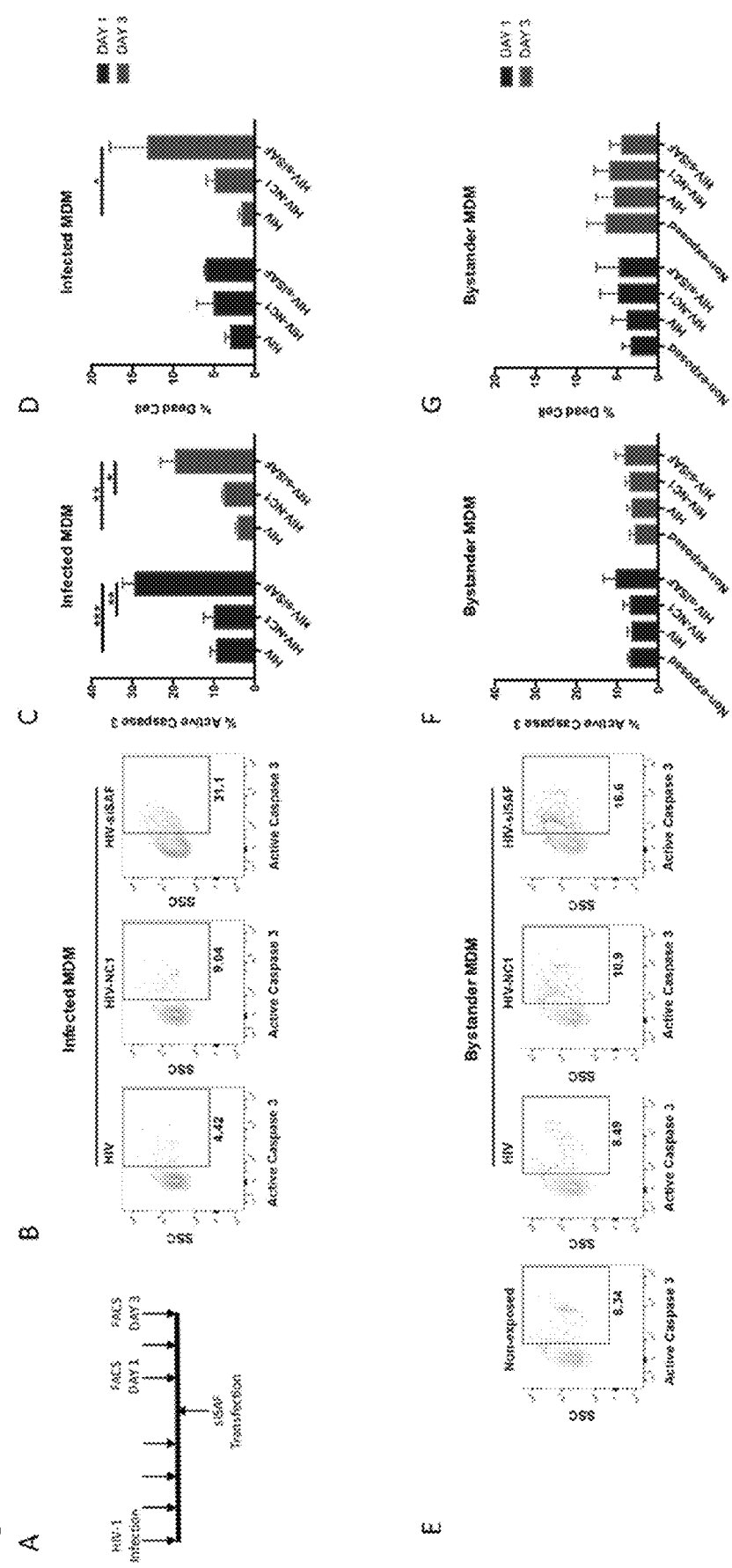

FIG. 3. Effect of siSAF treatment on apoptosis of HIV-1 infected MDMs. (A) Schematic presentation of the experiment timeline. MDMs were transfected with negative-control siRNA (NC1) or siSAF 4 days after infection with HIV-1 virus and analyzed for induction of apoptosis and cell death on day 1 and day 3 post transfection. Each arrow indicates a day. (B and E) Representative flow cytometry plots showing active caspase 3 staining of HIV-1 infected (B) or non-exposed and bystander (E) MDMs with or without siRNA treatment, as indicated above the panel. (C and F) The percentage of active caspase 3 positive cells (mean±SEM) was determined by flow cytometry staining with CellEvent caspase 3/7 green detection reagent in virus infected (C) or non-exposed and bystander (F) MDMs on day 1 (blue bar) and day 3 (red bar) post siRNA-transfection (n=4). (D and G) The percentage of dead cells (mean±SEM) was determined by flow cytometry with fixable viability dye eFluor506 in virus infected (D) or non-exposed and bystander (G) MDMs on day 1 (blue bar) and day 3 (red bar) post siRNA-transfection (n=4). HIV=virus infected and untreated, HIV-NC1=virus infected and negative-control siRNA NC1 treated, HIV-siSAF=virus infected and siSAF treated. Significance of difference among groups determined by one-way ANOVA is indicated above the groups, *=p<0.05, =p<0.01 and *=p<0.001.

Figure 4:
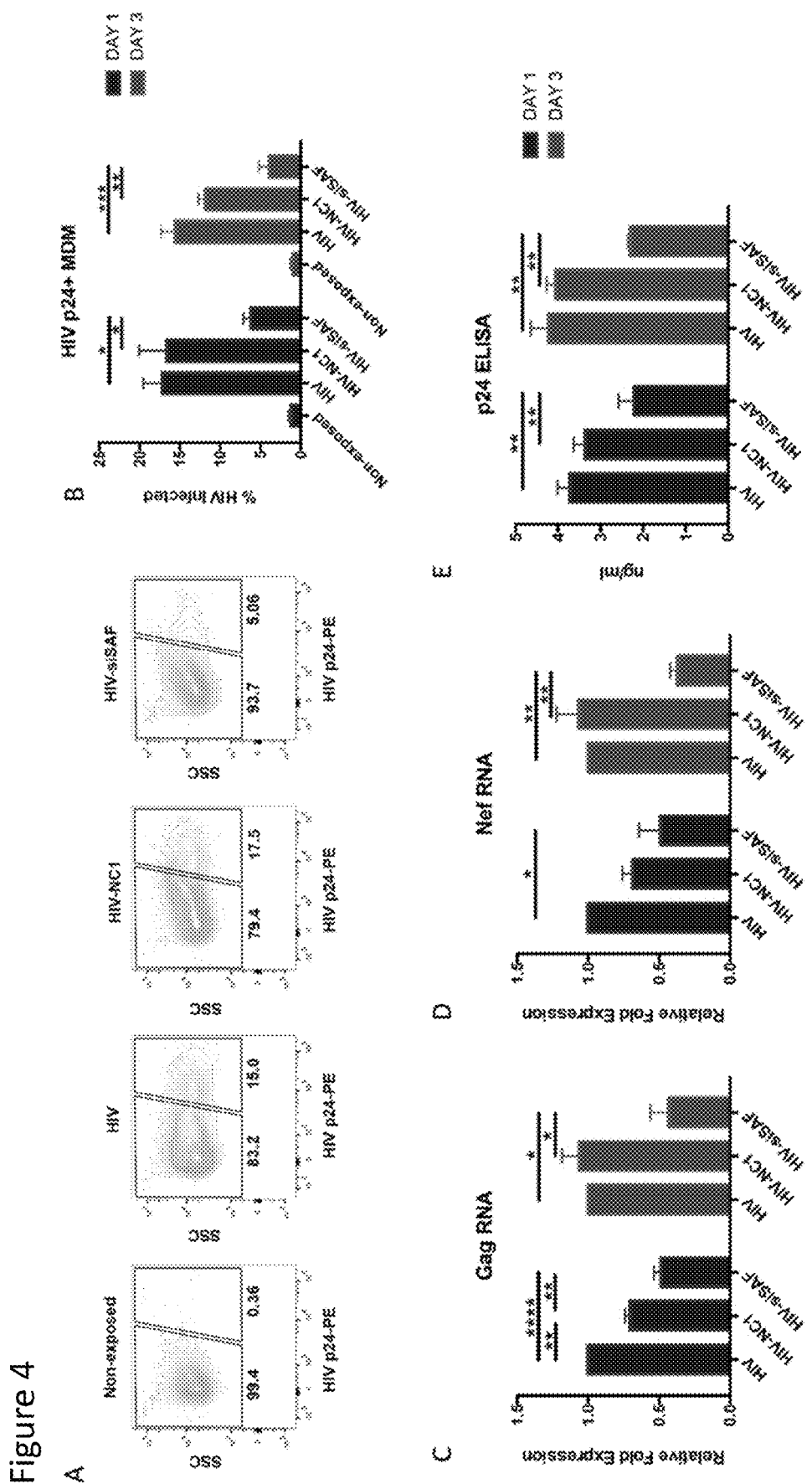

FIG. 4. Effect of siSAF treatment on HIV-1 infection in MDMs. (A) Representative flow cytometry plots showing p24-positive HIV-1 infected cells in virus non-exposed and virus infected MDMs with or without siRNA treatment, as indicated above the panel. (B) The percentage of viral p24-positive (mean±SEM) HIV-1 infected cells was determine by flow cytometry staining with PE-conjugated anti-p24 antibody in untreated, negative-control siRNA NC1 treated and siSAF treated MDMs on day 1 (blue bar) and day 3 (red bar) post siRNA-transfection (n=4). (C-D) Fold changes (mean±SEM) in expression of the viral Gag (C) and Nef (D) RNA was determined by quantitative real-time PCR in untreated, negative-control siRNA NC1 treated and siSAF treated MDMs on day 1 (blue bar) and day 3 (red bar) post siRNA-transfection (n=3). Expression levels of house-keeping genes GAPDH, U6 and 18S rRNA was used to normalize data. (E) The amount of viral p24 protein (mean±SEM) was determined by ELISA in the supernatant of HIV-1 infected cells in untreated, negative-control siRNA NC1 treated and siSAF treated MDMs on day 1 (blue bar) and day 3 (red bar) post siRNA-transfection (n=3). HIV=virus infected and untreated, HIV-NC1=virus infected and negative-control siRNA NC1 treated, HIV-siSAF=virus infected and siSAF treated. Significance of difference among groups determined by one-way ANOVA is indicated above the groups, *=p<0.05, =p<0.01 and *=p<0.001, ****=p<0.0001.

Figure 5:
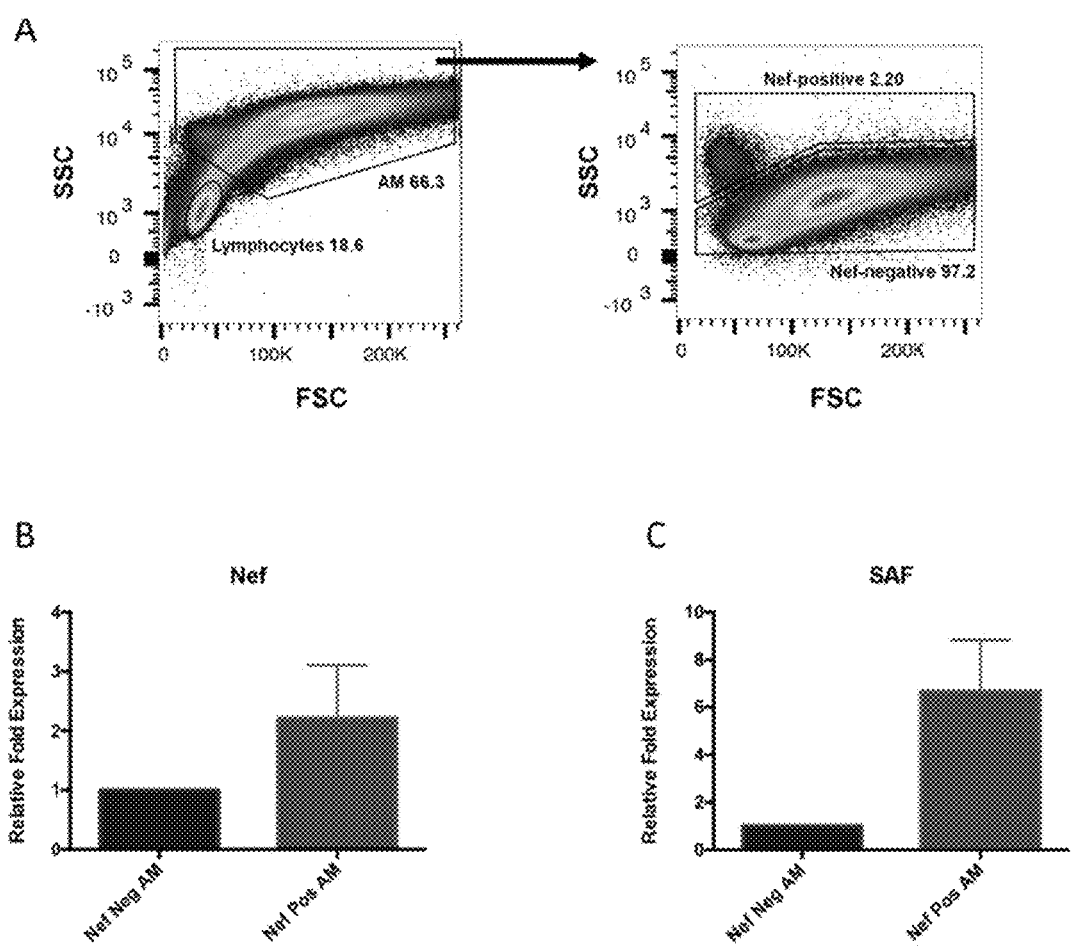

FIG. 5. Expression of lncRNA SAF in AMs from HIV-1 infected individuals. (A) Representative flow cytometry plots showing gating strategy for sorting Nef-positive and Nef-negative AMs. (B) Fold changes (mean±SEM) in expression of the HIV-1 Nef RNA was determined by quantitative real-time PCR in Nef-negative and Nef-positive AMs (n=3). (C) Fold changes (mean±SEM) in expression of the lncRNA SAF was determined by quantitative real-time PCR in Nef-negative and Nef-positive AMs (n=2).

Figure 6:
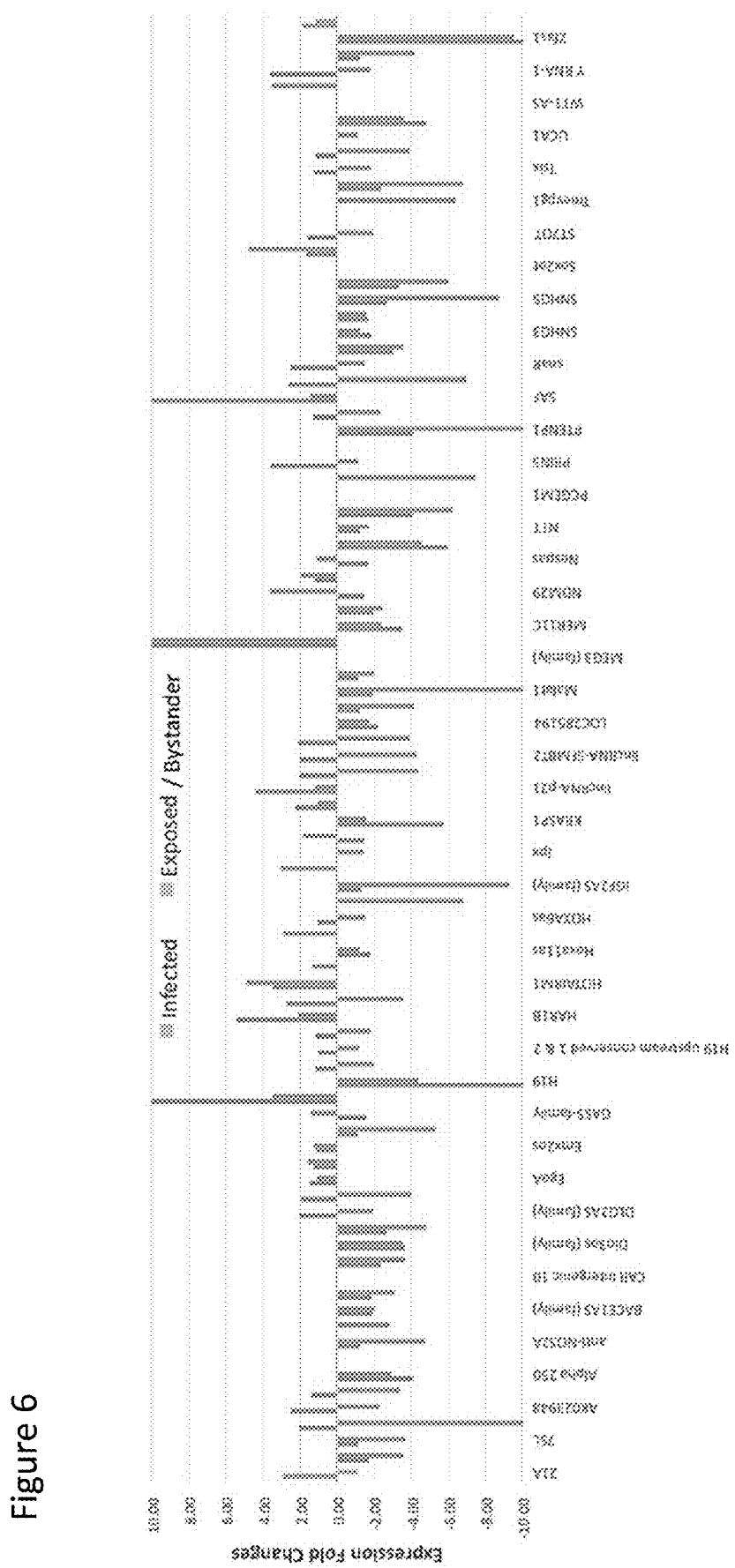

FIG. 6. lncRNA expression profile. A summary of the relative expressions of 71 lncRNAs in HIV-1 infected (red) and bystander (blue) MDMs compared to non-exposed MDMs.

Figure 7:
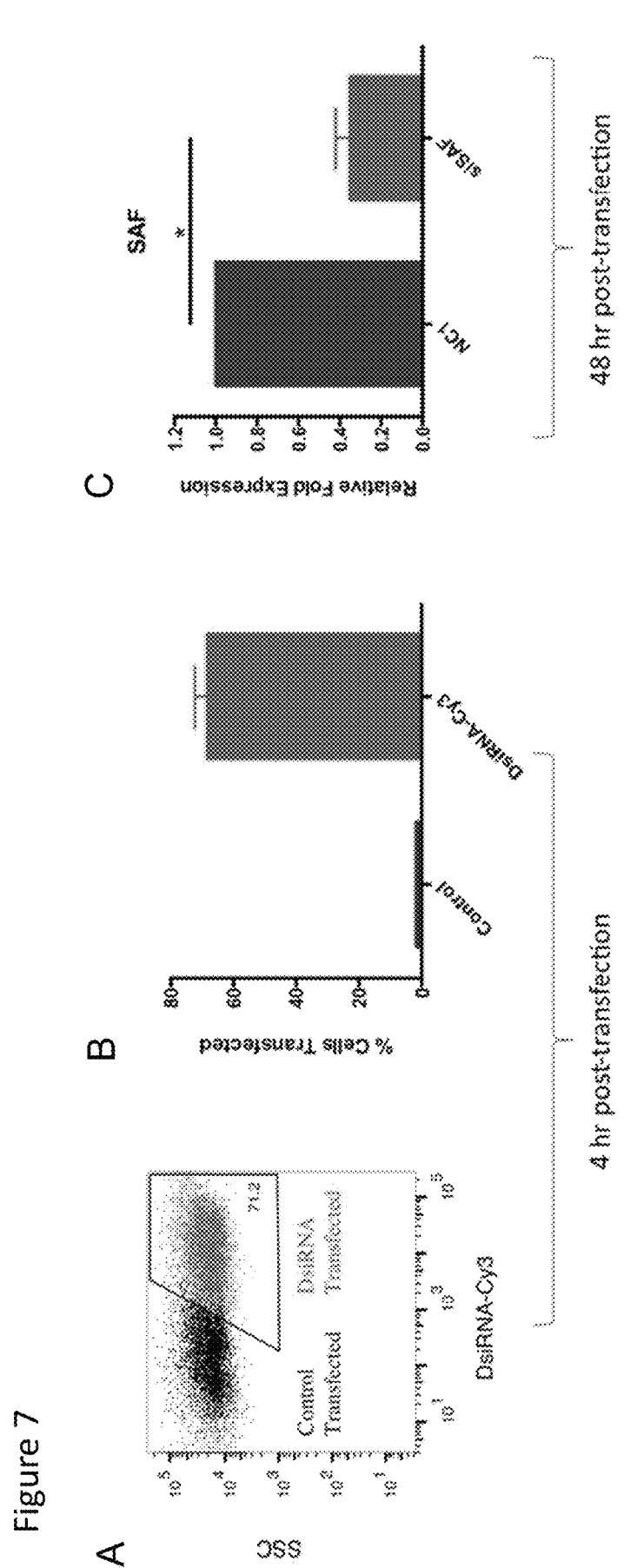

FIG. 7. siRNA transfection efficiency and siSAF treatment. (A) Representative flow cytometry plot showing transfection efficiency of Cy3-labelled DsiRNA in MDMs 4 hrs post transfection. (B) The percentage of cells (mean±SEM) showing Cy3 labelling in control transfected or Cy3-DsiRNA transfected MDMs at 4 hrs post transfection. (C) Fold changes (mean±SEM) in expression of the lncRNA SAF in control siRNA NC1 treated and siSAF treated MDMs at 48 hrs post transfection.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all nucleotide and amino acid sequences described herein, and every nucleotide sequence referred to herein includes its complementary DNA sequence, and also includes the RNA equivalents thereof, and vice versa. All sequences described herein, whether nucleotide or amino acid, include sequences having 50.0-99.9% identity, inclusive, and including all numbers and ranges of numbers there between to the first decimal point. The identity may be determined across the entire sequence, or a segment thereof that retains its intended function. Sequences associated with any database references, such as reference to a GenBank or other nucleotide and/or amino acid sequence database, are incorporated herein by reference as of the filing date of this application or patent.

In embodiments, the disclosure comprises selectively inducing cell death, such as apoptosis, of HIV infected macrophages by RNAi-mediated inhibition (including reducing the amount) of non-protein-coding regulatory elements, such as long non-coding RNAs (lncRNA). In embodiments, the lncRNA is anti-apoptotic lncRNA that regulates death receptor functions in the extrinsic pathway.

In embodiments, the lncRNA is SAF (FAS-AS1) or HOXA-AS2. The sequence of each of these lncRNA's is known in the art. For example, the sequence of human FAS-AS1 can be determined from the sequence under GenBank accession number NR 028371.1. The sequence of human HOXA-AS2 be determined from the sequence under GenBank accession number NR—122069.1.

In one embodiment, an RNAi-based inhibition of expression of a lncRNA can be achieved using any suitable RNA polynucleotide that is targeted to the lncRNA (an RNAi agent). In embodiments, the RNAi agent comprises an RNA that can have a single stranded or double stranded confirmation, wherein at least one strand is complementary to the lncRNA. In another embodiment, microRNA (miRNA) targeted to the lncRNA can be used. In another embodiment, a ribozyme that can specifically cleave the lncRNA can be used. In one embodiment, small interfering RNA (siRNA) can be used. siRNA can be produced from a single RNA that forms a double stranded siRNA complex. As is known in the art, shRNAs adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. In embodiments, an shRNA polynucleotide used to suppress a lncRNA can comprise or consist of between 45-100 nucleotides, inclusive, and including all integers between 45 and 100. The portion of the shRNA that is complementary to the lncRNA can be from 16-30 nucleotides, inclusive, and including all integers between 16 and 30. In embodiments, expression vectors encoding one or more siRNA agents described herein may be used. In embodiments, the expression vector that encodes a produces one or both strands of an RNAi agent described herein. In embodiments, the expression vector comprises a recombinant viral vector that can express the RNAi agent(s). Suitable expression vectors include but are not necessarily limited to lentiviral vectors, adenovirus vectors, and adeno associated viral vectors. In embodiments, a composition comprising RNAi agent(s) described herein is delivered to the lungs, or another mucosal surface of the individual.

In embodiments, the first or second nucleic acid strands of the RNAi agent, or both first and second nucleic acid single strands, may be provided as an RNA or DNA analog, or an RNA/DNA hybrid. The analog may include modified nucleotides and/or modified nucleotide linkages. Suitable modifications and methods for making nucleic acid analogs are known in the art. Some examples include but are not limited to polynucleotides which comprise modified ribonucleotides or deoxyribonucleotides. For example, modified ribonucleotides may comprise methylations and/or substitutions of the 2' position of the ribose moiety with an —O— lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. In embodiments modified nucleotides comprise methyl-cytidine and/or pseudo-uridine. The nucleotides may be linked by phosphodiester linkages or by a synthetic linkage, i.e., a linkage other than a phosphodiester linkage. Examples of inter-nucleoside linkages in the polynucleotide agents that can be used in the disclosure include, but are not limited to, phosphodiester, alkylphosphonate, phosphorothioate, phosphorodithioate, phosphate ester, alkylphosphonothioate, phosphoramidate, carbamate, carbonate, morpholino, phosphate triester, acetamidate, carboxymethyl ester, or combinations thereof. In embodiments, the DNA analog may be a peptide nucleic acid (PNA).

In one approach, one strand of the RNAi agent, such as an siRNA, comprises or consists of the sequence:

(SEQ ID NO: 1)
5'-rCrCrGrUrGrArArGrGrCrArUrArArArArGrCrArArArCr
ATT-3', wherein bases are RNA bases (rA) and the last two Ts are DNA.

In an embodiment, the RNAi agent comprises one strand that comprises or consists of the sequence: 3'-UUGGCAC-UUCCGUAUUUUCGUUUGUAA-5' (SEQ ID NO:2).

In embodiments, the RNAi agent comprises a duplex of SEQ ID NO:1 and SEQ ID NO:2, which may include overhanging bases, such as the UU at the 3' end of SEQ ID NO:2. Thus, the term "duplex" includes complementary double stranded polynucleotides described herein, wherein the double stranded polynucleotides may comprise one, two, three, or more overhanging bases. Accordingly, a duplex as used herein comprises an siRNA agent as the RNAi agent.

In embodiments, the RNAi agent exerts its effects in macrophages only. In embodiments, the RNA is targeted to macrophages. In embodiments, the RNAi agent exerts its effects only in HIV infected macrophages. In embodiments, non-HIV infected cells, such as non-HIV infected macrophages, are referred to as "bystanders."

Any result obtained using a method described herein can be compared to any suitable reference, such as a known value, or a control sample or control value, suitable examples of which will be apparent to those skilled in the art, given the benefit of this disclosure. In embodiments, introducing an RNAi agent as described herein into a population of macrophages preferentially induces apoptosis of HIV infected macrophages, relative to apoptosis of macrophages, or other in the population that are not infected by HIV. Thus, apoptosis induced by an RNAi agent described herein occurs more frequently, and/or more quickly, and/or exclusively, in HIV infected macrophages relative to non-HIV infected macrophages. In embodiments, the disclosure facilitates inducing apoptosis in alveolar HIV infected macrophages.

In embodiments, an RNAi agent of this disclosure is administered in a therapeutically effective amount. For any such agent, the therapeutically effective amount, e.g., a dose, can be estimated initially either in cell culture assays or in animal models. An animal model can also be used to determine a suitable concentration range, and route of administration. Such information can then be used to determine useful doses and routes for administration in humans. A precise dosage can be selected by the individual physician in view of the patient to be treated. Dosage and administration can be adjusted to provide sufficient levels of the active moiety or to maintain the desired effect. Additional factors which may be taken into account include the stage of HIV infection, the age, weight and gender of the patient, desired duration of treatment, method of administration, time and frequency of administration, drug combination(s), reaction sensitivities, and tolerance/response to therapy. A therapeutically effective amount is an amount that reduces one or more signs or symptoms of a disease, and/or reduces the severity of the disease. A therapeutically effective amount may also inhibit or prevent the onset of a disease, or a disease relapse. In embodiments, a therapeutically effective amount is an amount that reduces or eliminates HIV infected macrophages, and/or reduces viral load as determined in a biological sample from an individual before and after treatment. In embodiments, the disclosure only induces apoptosis in HIV infected macrophages. Some or all HIV infected macrophages into which an RNAi agent described herein may be induced to undergo apoptosis.

In embodiments, the disclosure pertains to combatting any type of HIV infection, a non-limiting embodiment of which comprises HIV-1.

In embodiments, an individual to whom an RNAi agent described herein is administered is infected with HIV, or is at risk for being infected with HIV. In embodiments, administration of the RNAi agent inhibits HIV from being transmitted from one individual to another (e.g., from an HIV-positive woman to her child during pregnancy, labor or delivery, or breastfeeding, or between sexual partners, or between individuals who, for example, may share HIV contaminated needles). In embodiments, the disclosure comprises administering a composition of this invention to a female who is pregnant and is known to be infected or is at risk of being infected by HIV. Direct administration to a fetus or to a newborn who is infected or is at risk of being infected with HIV is also included.

RNAi agents for use in embodiments of the present disclosure can be provided in pharmaceutical compositions by combining them with any suitable pharmaceutically acceptable carriers, excipients and/or stabilizers. Examples of pharmaceutically acceptable carriers, excipients and stabilizer can be found in *Remington: The Science and Practice of Pharmacy* (2005) 21st Edition, Philadelphia, Pa. Lippincott Williams & Wilkins, the disclosure of which is incorporated herein by reference. For example, suitable carriers include excipients, or stabilizers which are nontoxic to recipients at the dosages and concentrations employed.

Administration of compositions comprising RNAi agents as described herein can be carried out using any suitable route of administration known in the art. For example, the compositions may be administered via intravenous, intramuscular, intraperitoneal, intracerobrospinal, subcutaneous, intra-articular, intrasynovial, oral, topical, or inhalation routes, depending on the particular HIV infection in question. The compositions may be administered parenterally or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be therapeutically indicated.

In embodiments, the RNAi agent(s) of the disclosure may be provided in a composition that facilitates targeting of macrophages. In embodiments, the composition comprises liposomes or a nanoparticle. In embodiments, the composition comprises formyl methionine-leucine-phenylalanine (fMLF) peptide-PEG derivatives. The composition may comprise one or more binding partners that bind with specificity to macrophages, including but not necessarily limited to antibodies and antigen binding fragments thereof which bind with specificity to macrophage specific markers, such as macrophage specific surface markers and/or receptors.

Compositions of this disclosure can be combined with any other antiretroviral therapy (ART), including but not limited to reverse transcriptase inhibitors, integrase inhibitors, protease inhibitors, HIV entry/fusion inhibitors, carbohydrate binding agents, PI3K/Akt blocking agents, anti-HIV cytokines, and the like, and also includes HIV neutralizing antibodies that are administered to the individual. In embodiments, combining an RNAi agent described herein with an ART produces a synergistic effect. The synergistic effect can comprise, for example, a reduction in viral load that is greater than the additive effects of using either agent alone.

In an embodiment, the invention provides a method comprising introducing one or more RNAi agents described herein to a population of macrophages. The population of macrophages into which the RNAi agent(s) are introduced may be in an individual, or isolated from the individual. In performance of this embodiment, the macrophages may first be isolated from an individual using conventional techniques. The agent may be administered to the isolated macrophages cells so as to specifically target the FAS-AS1 or HOXA-AS2, thereby reducing or eliminating HIV positive macrophages from the population via apoptosis. The disclosure includes HIV infected macrophages that include an RNAi agent described herein. Macrophages described herein include classically activated macrophages ($M_1$ macrophages), and alternatively activated macrophages ($M_2$ macrophages).

The following Examples are intended to illustrate, but not limit the scope of this disclosure.

Example 1

Figure 1:
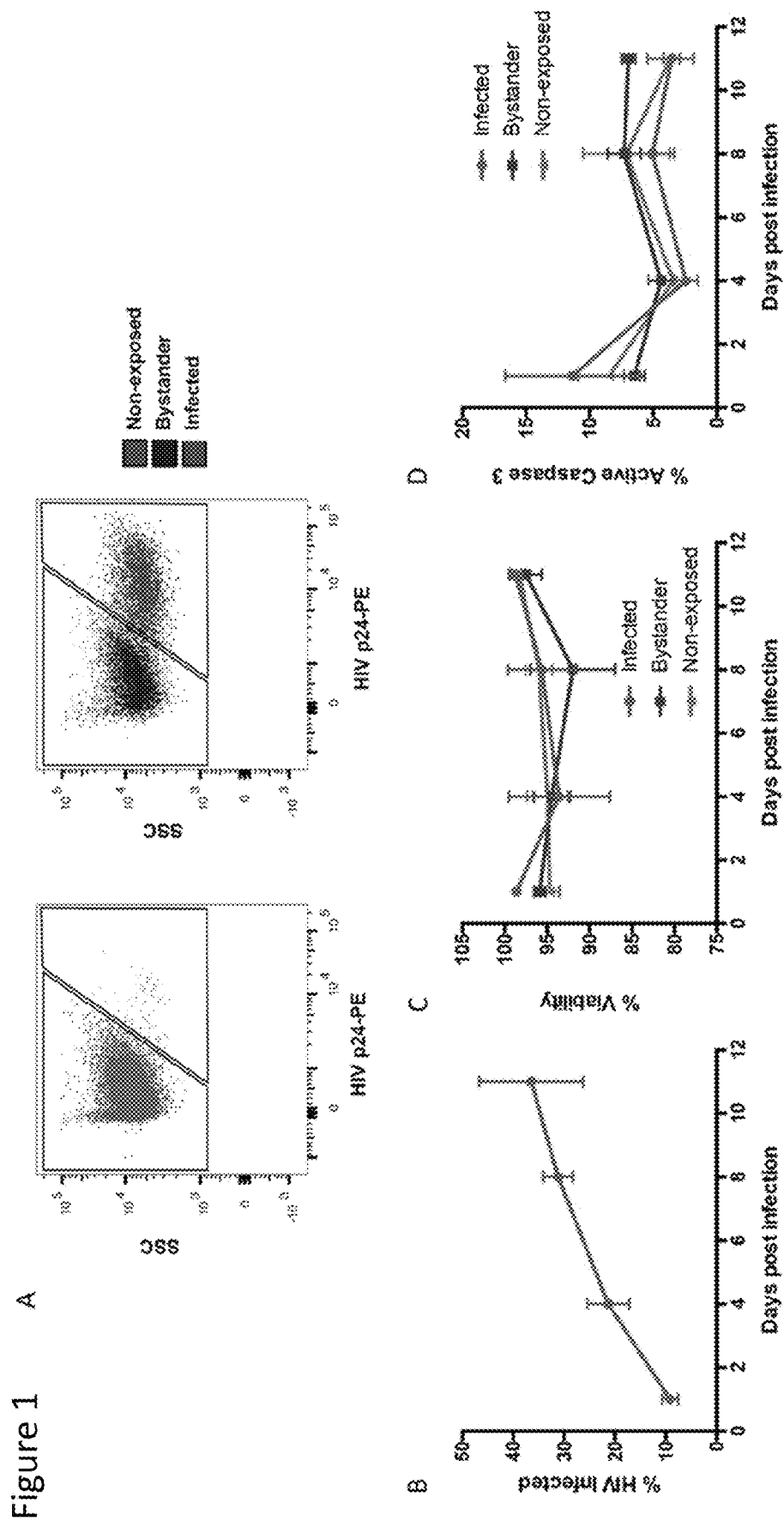

HIV-1 Infection of Human Monocyte-Derived-Macrophages Does Not Induce Apoptotic Cell Death To understand the dynamics of viral replication and apoptosis in HIV-1 infected primary macrophages, human MDMs were infected with a replication-competent VSV-G pseudotyped HXB3 virus expressing a R5-tropic BaL envelope (HXB3/BaL) and monitored up to 11 days post-infection (dpi) for viral infection and induction of apoptosis. As illustrated in FIG. 1A, HIV-1 infected macrophages were distinguished from uninfected bystanders by flow cytometric detection of intracellular expression of the viral capsid (p24) protein. The proportion of p24-positive HIV-1 infected cells within the virus infected culture increased progressively from 9.2% on 1 dpi to 36.5% on 11 dpi when the experiment was terminated (FIG. 1B). This demonstrates that HIV-1 establishes a productive and spreading viral infection in the primary macrophage culture. However, this productive infection did not increase cell death in the infected culture. Throughout the 11 days of infection, cell viability remained high in infected (mean, 97±1.7%), and in bystander (95±1.4%) or non-exposed (96±0.8%) cells (FIG. 1C). Level of active caspase 3, which is a final effector protease and an indicator of apoptosis, remained low in infected cells (2.5%-11.4%), at levels of expression comparable to those of bystander (4.4%-7.3%) and non-exposed cells (3.5%-8.5%) throughout the infection (FIG. 1D). Together, these data indicate that primary human macrophages support productive HIV-1 infection but resist the induction of apoptosis that is usually associated with HIV-1 infection of lymphocytes.

Example 2

Expression of lncRNA SAF is Up-Regulated in HIV-1 Infected MDMs

There is increasing evidence that lncRNAs play important roles in HIV-1 infection. However, most reports have focused on identifying those lncRNAs that impact viral replication (31, 32). The differential expression of lncRNAs in HIV-1 infected and exposed but uninfected macrophages has not been explored. To identify the lncRNAs that are differentially expressed in HIV-1 infected versus bystander cells, we infected MDMs with a replication-competent mCherry-reporter HIV-1 virus for 7 days and sorted HIV-1 infected (mCherry-positive) and bystander (mCherry-negative) MDMs. Uninfected, non-exposed MDMs were also processed through the cell sorter as control cells. The expression levels of 90 well-characterized lncRNAs, including a number of lncRNAs implicated in apoptosis were determined using a quantitative real-time PCR (qRT-PCR) based array. Out of the ninety, expression of 71 lncRNAs were detected in all three groups and therefore were used for further analysis (FIG. 6). Comparison of the lncRNA expression profile among non-exposed, bystander and virus infected MDMs revealed that 18 lncRNAs were up-regulated (≥2-fold) and 17 were down-regulated (≤2-fold) in HIV-1 infected MDMs, whereas in bystander cells only 6 were up-regulated. A considerable number of lncRNAs (36 out of 71) were down-regulated in the bystander MDMs (FIG. 2A). Changes in 19 lncRNAs followed a similar pattern in both virus-infected and bystander cells. A further examination of the 16 lncRNAs that were differentially expressed in HIV-1 infected MDMs (FIG. 2B) revealed that the change was most pronounced in the lncRNA SAF. This anti-apoptotic lncRNA had the highest increase in expression in HIV-1 infected cells but exhibited minimal up-regulation in the bystander MDMs, indicating that this variation was likely to be HIV-1 infection-specific. To further validate this lncRNA profiler array data, we measured SAF expression in HIV-1 infected, bystander and non-exposed cells using a different set of published qRT-PCR primers (37) in 4 independent MDM cultures. Consistent with the lncRNA profiler data, the independent qRT-PCR results (FIG. 2C) confirmed that SAF expression is significantly elevated in HIV-1 infected cells compared to bystander or virus non-exposed control MDMs.

Example 3

Inhibition of lncRNA SAF Induces Apoptosis in HIV-1 Infected MDMs

The lncRNA SAF has been shown to protect cells from apoptotic cell death (38, 39). To test if the lncRNA SAF is directly involved in the protection of HIV-1 infected MDMs against virus induced apoptosis, we used siRNA to reduce SAF expression levels in MDMs. Using Viromer Blue transfection reagent and a Cy3-labelled siRNA, we achieved an average transfection efficiency of about 70% in MDMs (FIGS. 7A & 7B). Transfection of MDMs with siSAF resulted in nearly a 3-fold reduction in SAF lncRNA level compared to a negative-control siRNA (NC1) treated cells, demonstrating that SAF lncRNA level in MDM can be effectively manipulated with siRNAs (FIG. 7C). Next, to assess how down-regulation of SAF expression in HIV-1 infected MDMs impacts apoptosis, we infected MDMs with VSV-G pseudotyped HIV-1 (HXB3/BaL) virus, allowed the infection to establish for 4 days and then treated the MDMs with either siSAF or control NC1 siRNA (FIG. 3A). As shown in FIGS. 3B and 3C, control NC1 siRNA treatment of MDMs did not have a substantial effect on active caspase 3 level, but siSAF treatment led to a significant induction in active caspase 3 in HIV-1 infected MDMs compared to untreated or NC1 control siRNA treated MDMs. After 1 day of transfection, there were approximately 3-fold more apoptotic cells within HIV-1 infected MDMs in siSAF treated culture than control NC1 treated or untreated MDMs (FIG. 3C). On day 3 post-transfection, although the level of apoptotic cells was still significantly higher among HIV-1 infected MDMs in siSAF treated culture, the effect of siSAF appeared to wane (FIG. 3C). In contrast to HIV-1 infected MDMs, active caspase 3 levels in neither the non-exposed nor the bystander cells were significantly affected by the siSAF treatment (FIGS. 3E and 3F). Although siSAF treatment led to a rapid induction of active caspase 3 on day 1, significant loss of complete cell viability in HIV-1 infected MDMs was only observed on day 3 post transfection, which is consistent with the progressive nature of the apoptotic cell death (FIG. 3D). Virus non-exposed and bystander cells again did not show any increase in cell death due to siSAF treatment (FIG. 3F). These data strongly indicate that siSAF treatment can induce apoptosis and consequently cell death specifically in HIV-1 infected macrophages while the uninfected bystander cells remain largely unaffected.

Example 4

Inhibition of lncRNA SAF Reduces HIV-1 Infection Burden in MDMs

As siSAF treatment rendered HIV-1 infected MDMs significantly more prone to apoptosis mediated cell death, we examined how this affected total HIV-1 viral burden in the MDM culture. We assessed this first by identification of HIV-1 p24-positive cells within the culture and observed that the proportion of virus infected cells was reduced significantly on day 1 post siSAF treatment (FIGS. 4A and 4B). The effect was even further pronounced by day 3 post-transfection when proportion of HIV-1 infected cells in siSAF treated culture was about 67-75% lower than control NC1 treated or untreated cultures, respectively (FIG. 4B). We then quantified HIV-1 viral RNA transcript levels in the cells to compare ongoing viral replication in the MDM cultures. As shown in FIGS. 4C and 4D, levels of both Gag and Nef viral RNA were significantly reduced in siSAF treated MDMs as early as day 1 post-transfection and remained low for 3 days. Interestingly, the control NC1 siRNA treatment also appeared to somewhat reduce the viral RNA levels on day 1, but the RNA levels recovered to that of untreated cells by day 3 post-transfection. Finally, we assessed the effect of siSAF treatment on virus production and spreading by measuring virion-associated p24 protein in the culture supernatant. Consistent with a reduced viral RNA transcript level, the amount of viral p24 protein was significantly decreased in the culture supernatant by day 1 and remained so for at least 3 days post-transfection (FIG. 4E). These results determine that siSAF treatment leads to a marked reduction in HIV-1 replication and total viral burden in the MDM culture.

Example 5

Expression of lncRNA SAF is Enhanced in HIV-1 Infected Human Alveolar Macrophages To determine if the alterations in SAF expression that is observed in MDMs also occurs in vivo during HIV-1 infection, we measured its expression in tissue-resident lung alveolar macrophages (AM) in HIV-1 infected individuals. Lung AMs in HIV-1 infected individuals have previously been shown to harbor the virus and viral RNA has been detected by fluorescent in-situ hybridization (FISH) and PCR-based assays (14). We obtained AMs from three HIV-1 infected, anti-retroviral therapy naïve individuals by bronchoalveolar lavage (BAL). Following a previously described method (14, 40), HIV-1 infected AMs within the BAL cells were detected and flow-sorted based on FISH-staining with fluorescent (Quasar 670)-labelled HIV-1 Nef probes (FIG. 5A). As reported earlier, HIV-1 infection was observed more frequently in small AMs. Nef probe-positive AMs showed in a 2 to 3-fold higher level of Nef RNA transcripts in the cells as detected by qRT-PCR (FIG. 5B), indicating a similar enrichment in virus infected cells within the Nef-positive AMs following the flow cytometry sorting. When we compared the levels of expression of the lncRNA SAF, we found that SAF RNA transcripts were approximately 6-fold more abundant in Nef-positive cells in comparison to the Nef-negative AMs in two of the three individuals (FIG. 5C). Expression of SAF could not be compared in the third individual as it was undetectable by PCR amplification in the Nef-positive cells. These data indicate that during natural HIV-1 infection, the virus induces a comparable enhancement in SAF expression in human lung macrophages to that observed in MDMs in vitro. This finding also indicates that similar to MDMs, the lncRNA SAF has a potential anti-apoptotic role in AMs during HIV-1 infection. Thus, it is expected that the data presented in this disclosure will be effective in inducing apoptosis in HIV infected macrophages in human individuals.

It will be recognized from the foregoing that it has become increasingly evident that lncRNAs play an important role in the virus-host interaction and pathogenesis. In the context of HIV-1 infection, studies on lncRNA expression and their role in viral pathogenesis have so far been limited to viral infection of lymphoid or monocytic cell lines (31, 32). Furthermore, most studies compared HIV-1 infected cultures as a whole to that of uninfected cultures without exploring the potential changes in uninfected bystander cells that were nonetheless exposed to the virus. Since only a fraction of the virus exposed cells become productively infected with HIV-1, which is particularly true of macrophages, this approach would fail to discriminate between HIV-1 infected and bystander cells within the same culture. In the present disclosure, the impact of HIV-1 infection on lncRNA expression in a primary human cell of myeloid origin is demonstrated, and has also delineated the differences between virus infected and bystander cells. These two cell subsets showed dramatic differences upon exposure to HIV-1 virus. Only 19 lncRNAs shared a similar pattern of expression in both infected and bystander MDMs when compared to virus non-exposed MDMs. In contrast, most of the differentially expressed lncRNAs were up-regulated in HIV-1 infected MDMs, while exposed but uninfected bystander cells showed a pattern of down-regulation in such lncRNA expression. Although results presented herein are obtained by targeting SAF, which was the most up-regulated lncRNA; the second-most up-regulated lncRNA on the list was lincRNA-p21 that has recently been shown to play an important anti-apoptotic role during HIV-1 infection in culture (41), and targeting the lincRNA-p21 is encompassed by this disclosure. These findings elucidate how HIV-1 cellular infection status differentially affects lncRNA expression levels and emphasizes the importance of distinguishing between the infected and bystander cell subsets during studies of virus induced alterations in cellular pathways.

The lncRNA that was markedly affected by HIV-1 infection in MDMs was SAF (FAS-AS1). It is a 1.5 kb antisense lncRNA that is transcribed from the intron 1 region of the FAS gene (37). Expression of this lncRNA has been shown to prevent apoptosis by inducing alternative splicing of the FAS gene and thereby increasing production of soluble FAS from the cells (39). Data presented in this disclosure revealed that expression of this anti-apoptotic lncRNA SAF was significantly up-regulated in HIV-1 infected MDMs compared to bystander and non-exposed cells. A similar increase in SAF expression was also observed in HIV-1 infected AMs. In contrast to the findings in MDMs and AMs, expression of SAF lncRNA is reportedly decreased in HIV-1 infected T cells that are susceptible to virus induced cell death (32). This suggests that the anti-apoptotic lncRNA SAF is differentially regulated in macrophages and T lymphocytes during HIV-1 infection. This observation is consistent with the respective fate of these two cell types following HIV-1 infection as delayed activation of caspase 3 and apoptosis has also been associated with the impaired killing of HIV-1 infected macrophages relative to $CD4^+$ T cells by cytotoxic T cells (42). Moreover, bystander MDMs did not show a statistically significant increase in SAF expression in comparison to virus non-exposed control MDMs. This indicates that active viral infection and/or replication, rather than mere exposure to the HIV-1 virion, is necessary for induction of SAF lncRNA-dependent cell survival in macrophages.

Data presented herein demonstrate that HIV-1 mediated evasion of apoptosis in macrophages can be effectively negated by siRNA-mediated down-regulation of SAF expression. Such genetic modulation was very specific as the siRNA treatment induced apoptosis and subsequent loss of cell viability in the HIV-1 infected macrophages alone, leaving the bystander and non-exposed cells unaffected. The results also showed that this selective targeting of the infected cells can result in a significant decline in viral burden. Indeed, transfection of MDMs with siSAF reduced HIV-1 replication and virus production by nearly 2-fold within one day of treatment. On day 1 post transfection, an increase in cellular active caspase 3 and induction of apoptotic pathway was adequate to inhibit virus replication even without an increase in complete loss of cell viability. With a siRNA based treatment approach, which would be transient, a single round of transfection was sufficient to sustain reduced levels of virus infection for at least 3 days. The disclosure includes enhancing the described effects through multiple rounds of treatment. The in vivo significance of these results are supported by the demonstration that comparable up-regulation of the lncRNA SAF is observed in HIV-1 infected alveolar macrophages from the lungs of HIV-1-positive individuals. These alveolar macrophages are now known to originate from fetally-derived stem cells and are capable of extended live-span measurable in years. Such long-lived tissue resident macrophages are considered to be good candidates as reservoirs for HIV-1 persistence, especially if stabilized by anti-apoptotic programs such as driven by the lncRNA SAF. Thus, the present disclosure highlights the role of lncRNAs as an important regulator in the cellular response to HIV-1 infection and pathogenesis as well as the potential of targeting long non-coding RNAs such as SAF as a therapeutic intervention specifically aimed towards HIV-1 infected long-lived reservoirs.

Example 6

The following materials and methods were used to obtain the results described in this disclosure.

Virus Production and Infection

The HIV-1 infectious molecular clone, pWT/BaL (HXB3/BaL, Catalog 11414) was obtained from the NIH AIDS Reagent Program. The plasmid encoding HIV-1 molecular clone NL43-IRES-mCherry with R5-tropic env (BaL) was generated by replacing the eGFP sequence with that of mCherry in the original plasmid pBR43IeG-nef+ R5env. Replication competent VSV-G pseudotyped HIV-1 virus was prepared by co-transfecting 293FT cells with the respective HIV-1 molecular clone and VSV-G expression plasmid using Lipofectamine 3000 reagent (Life Technologies). Transfection media was replaced with fresh antibiotic free DMEM media 8 hrs post transfection. After 72 hrs, cell culture supernatant containing HIV-1 virus was harvested, centrifuged to remove cell debris, passed through 0.45 µm filter and stored at −80° C. in aliquots. Titer of the virus stock was determined by p24 ELISA (RETROtek HIV-1 p24 antigen ELISA kit, ZeptoMetrix) and 50 ng/ml of virus was used to infect MDMs.

MDM Differentiation and siRNA Transfection

Human monocytes were obtained from peripheral blood mononuclear cells of healthy individuals by counter-current centrifugal elutriation with an average purity of >97% (Elutriation core facility, University of Nebraska Medical Center). Monocytes were maintained in DMEM media supplemented with 10% human serum, 100 U/ml penicillin and 100 µg/ml streptomycin (Invitrogen). Cells were cultured at 37° C. with 6% $CO_2$ for 7-8 days to fully differentiate into macrophages (MDMs).

For siRNA treatment, $1.5 \times 10^6$ MDMs were transfected with either 10 nM each of three DsiRNAs targeted to SAF (hs.Ri.FAS-AS1.13, IDT) or a non-specific control, NC1 (negative control DsiRNA, IDT) using Viromer Blue transfection reagent (Lipocalyx) according to manufacturer's instructions. Transfection efficiency was monitored with a Cy3-labelled DsiRNA (IDT) control.

lncRNA Profiling and Quantitative Real-Time PCR

For comparative lncRNA expression analysis of infected and bystander cells, fully differentiated MDMs were infected with the replication competent VSV-G pseudotyped NL43-IRES-mCherry-Bal virus. On day 7 post-infection, cells were harvested by gentle scrapping following a 10-minute incubation in cold PBS, washed once and processed with a Bio-rad S3 cell sorter to separate mCherry-positive HIV-1 infected and mCherry-negative bystander cells. Similar to the HIV-1 infected culture, virus non-exposed MDMs were also passed through the cell sorter and recovered as mCherry negative as an experimental control. Total RNA was extracted from sorted cells using Trizol reagent (Invitrogen) according to manufacturer's instructions, followed by DNase treatment (Turbo DNA-free kit, Invitrogen) to remove genomic DNA. The same amount of RNA was used for cDNA synthesis and subsequent quantification of lncRNA expression using the Human LncRNA Profiler qPCR Array kit (System Bioscience) and ABI 7500 Fast Real-time PCR system (Applied Bioscience) in accordance to the manufacturer's protocol. Expression of SAF lncRNA was further independently verified with previously published (37) primer sets (Forward primer: CAT CTC AGC CTC TTG GTG TAA (SEQ ID NO:3) and Reverse primer: ATG GGA GAT ATG GGA TTG AAC) (SEQ ID NO:4) and iTaq Universal SYBR Green Supermix (Bio-Rad). HIV-1 viral transcripts were quantified by qRT-PCR of Gag (Forward primer: AAG CAC TGG GAC CAG GAG C (SEQ ID NO:5)) and Reverse primer: TGG TAG CTG GAT TTG TTA CTT GGC (SEQ ID NO:6) and Nef (Forward primer: TAG TGT GAT TGG ATG GCC TGC (SEQ ID NO:7) and Reverse primer: ACA AGC ATT GTT AGC TGC TG (SEQ ID NO:8)) following a similar procedure. Expression of the house-keeping genes: GAPDH (Forward Primer: GAC AAG CTT CCC GTT CTC AG (SEQ ID NO:9) and Reverse primer: GAG TCA ACG GAT TTG GTC GT (SEQ ID NO:10)), U6 (Forward primer: CTC GCT TTG GCA CA (SEQ ID NO:11 and Reverse primer: AAC GCT TCA CGA ATT TGC GT SEQ ID NO:12)) and 18S rRNA (Forward primer: GGC CCT GTA ATT GGA ATG AGT C (SEQ ID NO:13) and Reverse primer: CCA AGA TCC AAC TAC GAG CTT (SEQ ID NO:14)) was used for normalization of qRT-PCR expression data.

Flow-Cytometry for HIV-1 p24 and Detection of Apoptosis

MDMs were harvested by gentle scrapping following a 10-minute incubation in cold PBS. Cells were stained for intracellular active caspase-3/7 enzyme using the CellEvent Caspase-3/7 Green Detection reagent (Invitrogen) according to the manufacturer's instruction with some modifications. Briefly, cells were resuspended in 1 ml PBS to which 1 µl CellEvent caspase-3/7 reagent was added and then incubated at 37° C. for 30 minutes. During the last 10 minutes of incubation 1 µl of Fixable Viability Dye eFluor 506 (eBioscience) was added to the cells. Thereafter, the cells were washed with PBS and fixed and permeabilized using 1X Cytofix/cytoperm solution (BD Bioscience) for 30 minutes. For detection of HIV-1 infected MDMs, the cells were then stained with an antibody against the HIV-1 core protein p24 (KC57-RD1, Beckman Coulter) for 30 minutes at room temperature. Finally, the cells were fixed in 1% paraformaldehyde in PBS and analyzed with a BD LSRII flow cytometer. Flow cytometry data was analyzed using FlowJo software.

Study Subjects and Bronchoalveolar Lavage

Bronchoalveolar lavage (BAL) was obtained from three HIV-positive, anti-retroviral treatment naive individuals (aged ≥18 yrs) at the Queen Elizabeth Central Hospital in Blantyre, Malawi. Age, gender, plasma viral load and CD4 T cell counts of the study participants at the time of bronchoscopy are listed in Table 1.

TABLE 1

| Subject ID | Age (years) | Gender | Plasma viral load (copies/ml) | CD4 T cell count (cells/µl) |
|---|---|---|---|---|
| AMAC282 | 20 | Female | 24,626 | 878 |
| AMAC283 | 33 | Female | 5,582 | 490 |
| AMAC292 | 40 | Female | 8,617 | 311 |

The study received ethical approval from the research ethics committees of the College of Medicine, Malawi (Research protocol P.10/08/708), the Liverpool School of Tropical Medicine, UK (Research protocol 08.54) and Cornell University, USA (Research protocol 908000698). All study participants provided written informed consents.

FISH Staining and Flow Cytometry Sorting of Alveolar Macrophages

FISH staining for HIV-1 Nef RNA in lung alveolar macrophages were carried out as previously described (14, 40). Stained macrophages were sorted into Nef-positive and Nef-negative cells using a BD FACS Aria cell sorter.

Statistical Analysis

Statistical analysis was performed using GraphPad Prism software. Unless otherwise indicated, one-way ANOVA with Tukey's multiple comparison test was used for all statistical analysis and a p-value below 0.5 was considered significant.

REFERENCES

This reference listing is not intended to indicate that any particular reference is material to patentability.
1. Fahey J L, et al. (1990) The prognostic value of cellular and serologic markers in infection with human immunodeficiency virus type 1. *N Engl J Med* 322 (3):166-172.
2. Margolick J B & Donnenberg A D (1997) T-cell homeostasis in HIV-1 infection. *Semin Immunol* 9 (6):381-388.
3. Moir S, et al. (2010) B cells in early and chronic HIV infection: evidence for preservation of immune function associated with early initiation of antiretroviral therapy. *Blood* 116 (25):5571-5579.
4. Alter G, et al. (2005) Sequential deregulation of NK cell subset distribution and function starting in acute HIV-1 infection. *Blood* 106 (10):3366-3369.
5. Donaghy H, et al. (2001) Loss of blood CD11c(+) myeloid and CD11c(−) plasmacytoid dendritic cells in patients with HIV-1 infection correlates with HIV-1 RNA virus load. *Blood* 98 (8):2574-2576.
6. Brenchley J M, et al. (2004) CD4+ T cell depletion during all stages of HIV disease occurs predominantly in the gastrointestinal tract. *J Exp Med* 200(6):749-759.
7. Ho D D, et al. (1995) Rapid turnover of plasma virions and CD4 lymphocytes in HIV-1 infection. *Nature* 373 (6510):123-126.
8. Verani A, Gras G, & Pancino G (2005) Macrophages and HIV-1: dangerous liaisons. *Mol Immunol* 42 (2): 195-212.
9. Sieweke M H & Allen J E (2013) Beyond stem cells: self-renewal of differentiated macrophages. *Science* 342 (6161): 1242974.
10. Jenkins S J, et al. (2011) Local macrophage proliferation, rather than recruitment from the blood, is a signature of TH2 inflammation. *Science* 332 (6035):1284-1288.
11. Hashimoto D, et al. (2013) Tissue-resident macrophages self-maintain locally throughout adult life with minimal contribution from circulating monocytes. *Immunity* 38 (4):792-804.
12. Guilliams M, et al. (2013) Alveolar macrophages develop from fetal monocytes that differentiate into long-lived cells in the first week of life via GM-CSF. *J Exp Med* 210 (10):1977-1992.
13. Gordon S & Taylor P R (2005) Monocyte and macrophage heterogeneity. *Nat Rev Immunol* 5 (12):953-964.
14. Jambo K C, et al. (2014) Small alveolar macrophages are infected preferentially by HIV and exhibit impaired phagocytic function. *Mucosal Immunol* 7 (5):1116-1126.
15. Jordan C A, Watkins B A, Kufta C, & Dubois-Dalcq M (1991) Infection of brain microglial cells by human immunodeficiency virus type 1 is CD4 dependent. *J Virol* 65 (2):736-742.
16. Joseph S B, Arrildt K T, Sturdevant C B, & Swanstrom R (2015) HIV-1 target cells in the CNS. *J Neurovirol* 21 (3):276-289.
17. Housset C, et al. (1990) Immunohistochemical evidence for human immunodeficiency virus-1 infection of liver Kupffer cells. *Hum Pathol* 21 (4):404-408.
18. DiNapoli S R, et al. (2017) Tissue-resident macrophages can contain replication-competent virus in antiretroviral-naive, SIV-infected Asian macaques. *JCI Insight* 2 (4): e91214.
19. Koenig S, et al. (1986) Detection of AIDS virus in macrophages in brain tissue from AIDS patients with encephalopathy. *Science* 233 (4768):1089-1093.
20. Avalos C R, et al. (2016) Quantitation of Productively Infected Monocytes and Macrophages of Simian Immunodeficiency Virus-Infected Macaques. *J Virol* 90 (12): 5643-5656.
21. Honeycutt J B, et al. (2016) Macrophages sustain HIV replication in vivo independently of T cells. *J Clin Invest* 126 (4):1353-1366.
22. Carter C A & Ehrlich L S (2008) Cell biology of HIV-1 infection of macrophages. *Annu Rev Microbiol* 62:425-443.
23. Chugh P, et al. (2007) Infection of human immunodeficiency virus and intracellular viral Tat protein exert a pro-survival effect in a human microglial cell line. *J Mol Biol* 366 (1):67-81.
24. Giri M S, Nebozhyn M, Showe L, & Montaner L J (2006) Microarray data on gene modulation by HIV-1 in immune cells: 2000-2006. *J Leukoc Biol* 80 (5):1031-1043.
25. Meyaard L, et al. (1992) Programmed death of T cells in HIV-1 infection. *Science* 257 (5067):217-219.
26. Terai C, Kornbluth R S, Pauza C D, Richman D D, & Carson D A (1991) Apoptosis as a mechanism of cell death in cultured T lymphoblasts acutely infected with HIV-1. *J Clin Invest* 87 (5):1710-1715.
27. Barber G N (2001) Host defense, viruses and apoptosis. *Cell Death Differ* 8 (2):113-126.
28. Swingler S, Mann A M, Zhou J, Swingler C, & Stevenson M (2007) Apoptotic killing of HIV-1-infected macrophages is subverted by the viral envelope glycoprotein. *PLoS Pathog* 3 (9):1281-1290.
29. Cummins N W & Badley A D (2010) Mechanisms of HIV-associated lymphocyte apoptosis: 2010. *Cell Death Dis* 1:e99.
30. Badley A D, Sainski A, Wightman F, & Lewin S R (2013) Altering cell death pathways as an approach to cure HIV infection. *Cell Death Dis* 4:e718.
31. Imam H, Bano A S, Patel P, Holla P, & Jameel S (2015) The lncRNA NRON modulates HIV-1 replication in a NFAT-dependent manner and is differentially regulated by early and late viral proteins. *Sci Rep* 5:8639.
32. Zhang Q, Chen C Y, Yedavalli V S, & Jeang K T (2013) NEAT1 long noncoding RNA and paraspeckle bodies modulate HIV-1 posttranscriptional expression. *MBio* 4 (1):e00596-00512.
33. Su Y, et al. (2016) Regulatory non-coding RNA: new instruments in the orchestration of cell death. *Cell Death Dis* 7 (8):e2333.
34. Zhao H, Zhang X, Frazao J B, Condino-Neto A, & Newburger P E (2013) HOX antisense lincRNA HOXA-AS2 is an apoptosis repressor in all trans retinoic acid treated NB4 promyelocytic leukemia cells. *J Cell Biochem* 114 (10):2375-2383.
35. Zhou Y, et al. (2007) Activation of p53 by MEG3 non-coding RNA. *J Biol Chem* 282 (34):24731-24742.

36. Pickard M R, Mourtada-Maarabouni M, & Williams G T (2013) Long non-coding RNA GAS5 regulates apoptosis in prostate cancer cell lines. *Biochim Biophys Acta* 1832 (10):1613-1623.
37. Yan M D, et al. (2005) Identification and characterization of a novel gene Saf transcribed from the opposite strand of Fas. *Hum Mol Genet* 14 (11):1465-1474.
38. Villamizar O, et al. (2016) Fas-antisense long noncoding RNA is differentially expressed during maturation of human erythrocytes and confers resistance to Fas-mediated cell death. *Blood Cells Mot Dis* 58:57-66.
39. Villamizar O, Chambers C B, Riberdy J M, Persons D A, & Wilber A (2016) Long noncoding RNA Saf and splicing factor 45 increase soluble Fas and resistance to apoptosis. *Oncotarget* 7 (12): 13810-13826.
40. Wilburn K M, et al. (2016) Heterogeneous loss of HIV transcription and proviral DNA from 8E5/LAV lymphoblastic leukemia cells revealed by RNA FISH:FLOW analyses. *Retrovirology* 13 (1):55.
41. Barichievy S, et al. (2018) Viral Apoptosis Evasion via the MAPK Pathway by Use of a Host Long Noncoding RNA. *Front Cell Infect Microbiol* 8:263.
42. Clayton K L, et al. (2018) Resistance of HIV-infected macrophages to CD8(+) T lymphocyte-mediated killing drives activation of the immune system. *Nat Immunol* 19 (5):475-486.

What is claimed is:

1. A method for therapy for a human immunodeficiency virus (HIV) infection comprising administering to an individual in need thereof a therapeutically effective amount of an RNAi agent targeted to an anti-apoptotic long non-coding RNA (lncRNA) that is lncRNA SAF (FAS-AS1), the RNAi agent comprising a duplex comprising SEQ ID NO:1 and SEQ ID NO:2.

2. The method of claim 1, wherein the administering to the individual comprises introducing the RNAi agent into a population of macrophages in the individual, the population of macrophages comprising HIV infected macrophages.

3. The method of claim 2, wherein subsequent to introducing the RNAi agent the HIV infected macrophages undergo apoptosis.

4. A method for inducing apoptosis of HIV infected macrophages, the method comprising introducing into the HIV infected macrophages an RNAi agent targeted to an anti-apoptotic long non-coding RNA (lncRNA) that is lncRNA SAF (FAS-AS1) wherein the RNAi agent comprises a duplex comprising SEQ ID NO:1 and SEQ ID NO:2, wherein the HIV infected macrophages that comprise the RNAi agent undergo apoptosis.

5. The method of claim 4, wherein the HIV macrophages are present in a population of macrophages comprising macrophages that are not infected with the HIV, and wherein only the macrophages that are infected with the HIV undergo apoptosis.

* * * * *